(12) United States Patent
Ethier et al.

(10) Patent No.: US 6,366,351 B1
(45) Date of Patent: Apr. 2, 2002

(54) APPARATUS FOR DETECTING DEFECTS IN WOOD PROCESSED BY A PLANER

(75) Inventors: Daniel Ethier, Ste-Thérèse; Robert Lessard, St-Janvier, both of (CA)

(73) Assignee: Autolog Inc., Quebec (CA)

( * ) Notice: Subject to any disclaimer, the term of this patent is extended or adjusted under 35 U.S.C. 154(b) by 0 days.

(21) Appl. No.: 09/549,705

(22) Filed: Apr. 14, 2000

(30) Foreign Application Priority Data

Apr. 16, 1999 (CA) ............................................. 2268337

(51) Int. Cl.[7] ............................................. G01N 21/00
(52) U.S. Cl. .................................. 356/237.1; 356/237.2
(58) Field of Search ........................... 356/237.1, 237.2, 356/375, 376, 379, 381, 383, 384, 385, 386, 387; 198/782, 780, 826; 250/559.4, 559.42, 559.13, 559.45, 559.19, 559.22, 559.24, 559.27, 559.29; 382/108, 141, 286, 313, 325; 144/402–404, 246.1, 248.3, 248.4, 248.5, 248.7

(56) References Cited

U.S. PATENT DOCUMENTS

| 3,566,121 A | | 2/1971 | Myers ........................ 250/83.3 |
| 3,627,005 A | * | 12/1971 | Morton et al. ................. 144/39 |
| 3,687,260 A | * | 8/1972 | Willows ....................... 198/24 |
| 3,827,545 A | | 8/1974 | Buhayar ....................... 198/34 |
| 4,067,370 A | * | 1/1978 | Chang .................... 144/117 R |
| 4,078,592 A | * | 3/1978 | Standal .................... 144/208 R |
| 4,172,417 A | | 10/1979 | Fardeau et al. ............. 101/114 |
| 4,325,477 A | | 4/1982 | Heikinheimo ................ 198/461 |
| 4,356,045 A | * | 10/1982 | Elford et al. ................. 156/64 |
| 4,879,752 A | * | 11/1989 | Aune et al. ..................... 382/1 |
| 4,947,909 A | * | 8/1990 | Stroud ......................... 144/357 |
| 5,232,030 A | * | 8/1993 | Knerr et al. ............. 144/246 D |
| 5,252,836 A | * | 10/1993 | Matthews et al. .......... 250/571 |
| 5,365,812 A | * | 11/1994 | Harnden ........................ 83/34 |
| 5,506,914 A | * | 4/1996 | Baker ......................... 382/141 |
| 5,644,392 A | * | 7/1997 | Soest et al. ................. 356/237 |
| 5,676,238 A | * | 10/1997 | Saastamo ................. 198/502.2 |
| 5,765,617 A | * | 6/1998 | Mierau et al. .............. 144/387 |
| 5,918,653 A | * | 7/1999 | Knerr ......................... 144/404 |

OTHER PUBLICATIONS

R.W. Conners et al., "Machine Vision Technology for the Forest Products Industry", Computer, (Jul. 1997), pp. 43–48.
R.W. Conners et al., "Computer Vision Hardware System for Automating Rough Mills of Furniture Plants", SPIE vol. 1293, Applications of Artificial Intelligence V111, (1990), pp. 776–787 with Abstract.
R.W. Conners et al., "A machine vision system for automatically grading hardwood lumber", Industrial Metrology 2, (1992), pp. 317–342 with Abstract.

* cited by examiner

Primary Examiner—Frank G. Font
Assistant Examiner—Michael P. Stafira
(74) Attorney, Agent, or Firm—Sughrue Mion, PLLC

(57) ABSTRACT

An apparatus for detecting defects in wood which includes an inlet for loading a piece of wood in the apparatus, a scanning device for scanning and detecting defects in the piece of wood and an outlet for releasing the piece of wood from the apparatus. The inlet and outlet are each provided with at least one roller assembly which include a top and bottom roller. The roller assemblies are positioned relative to each other and the scanning device so that the piece of wood is maintained, at any time, by two points.

13 Claims, 4 Drawing Sheets

FIG. 4a
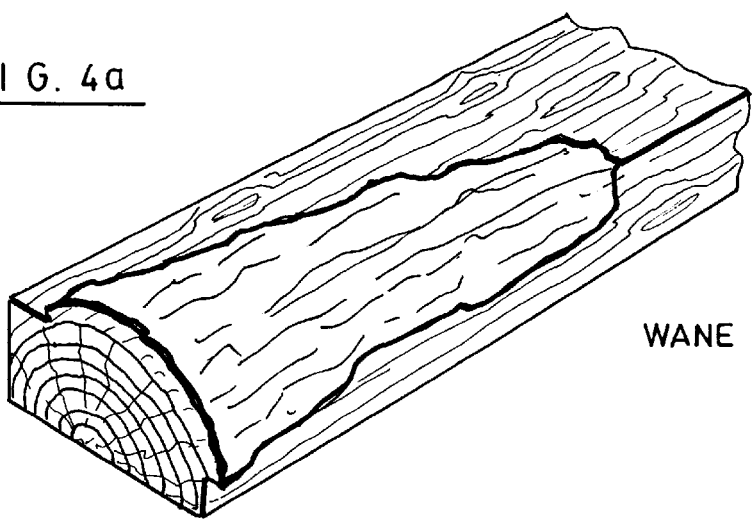
WANE
FIG. 4b
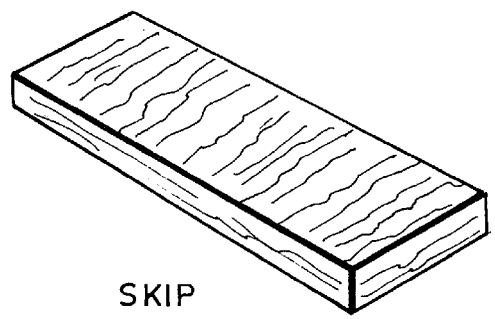
SKIP
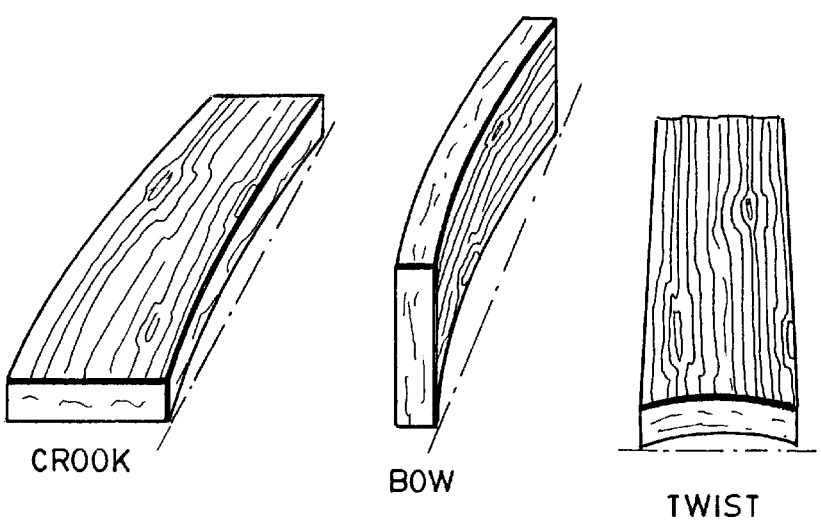
CROOK
BOW
TWIST
FIG. 4c     FIG. 4d     FIG. 4e

APPARATUS FOR DETECTING DEFECTS IN WOOD PROCESSED BY A PLANER

FIELD OF THE INVENTION

The present invention relates to an apparatus for detecting defects in wood, particularly wood which has been processed with a planer.

DESCRIPTION OF THE PRIOR ART

It is known presently to visually inspect pieces of wood after they have been processed with a planer, in order to categorise them. This process is labour-intensive and time consuming, and requires considerable experience in order to properly grade the wood. Defects such as wane, twist, crook, skip and bow are evaluated.

Canadian patent application no. 2,237,640 describes an apparatus and method for detecting surface defects. The apparatus includes surface shape detection means for obtaining profile trace data of at least one surface of the article at a cross-section, the profile trace data being referenced to a reference system, data processing means for deriving a base reference curve from generally rectangular portions of the profile trace data and defect detecting means comparing the trace data with the base reference curve to recognise a defect induced departure of the trace data with respect to the base reference curve and to produce a defect output signal.

However, the apparatus described in this application does not necessarily work as expected since there are no means provided to maintain the article in a given position while the article is being scanned. Accordingly, the error margin is considerable, and it is extremely difficult for the apparatus to provide accurate results.

SUMMARY OF THE INVENTION

It is an object of the invention to provide an apparatus for detecting defects which reduces the computational power required to properly analyse an article by maintaining the article in a predetermined position while it is being scanned.

In accordance with the invention, this object is achieved with an apparatus for detecting defects in wood comprising:

a frame comprising
an inlet for loading and conveying the piece of wood in the apparatus in the scanning direction,
an outlet for releasing the piece of wood from the apparatus;
scanning means located between the inlet and the outlet for scanning said piece of wood, the scanning means including an output for scanned data;
computer means operatively connected to the scanning means for receiving the scanned data and processing said data; and
control means for controlling the inlet and the scanning means and insuring proper synchronization.

The inlet and outlet of the apparatus according to the present invention each comprise at least one roller assembly. Each roller assembly is designed to hold two opposite surfaces of the piece of wood so that the piece of wood is conveyed between said roller assembly. The apparatus is characterized in that each roller assembly are positioned so that when the piece of wood passes by said scanning means, it is held and guided by at least two points.

Another object of the present invention is concerned with a method for detecting defects in wood by using the apparatus of the present invention.

BRIEF DESCRIPTION OF THE DRAWINGS

The present invention and its advantages will be more easily understood after reading the following non-restrictive description of preferred embodiments thereof, made with reference to the following drawings in which:

FIGS. 4a, 4b, 4c, 4d and 4e are schematic representations of the defects in wood the present invention can detect.

DESCRIPTION OF A PREFERRED EMBODIMENT OF THE INVENTION

The present invention is directed to an apparatus for detecting defects in wood. Such an apparatus is preferably placed at the output of a typical wood planer.

Figure 1:
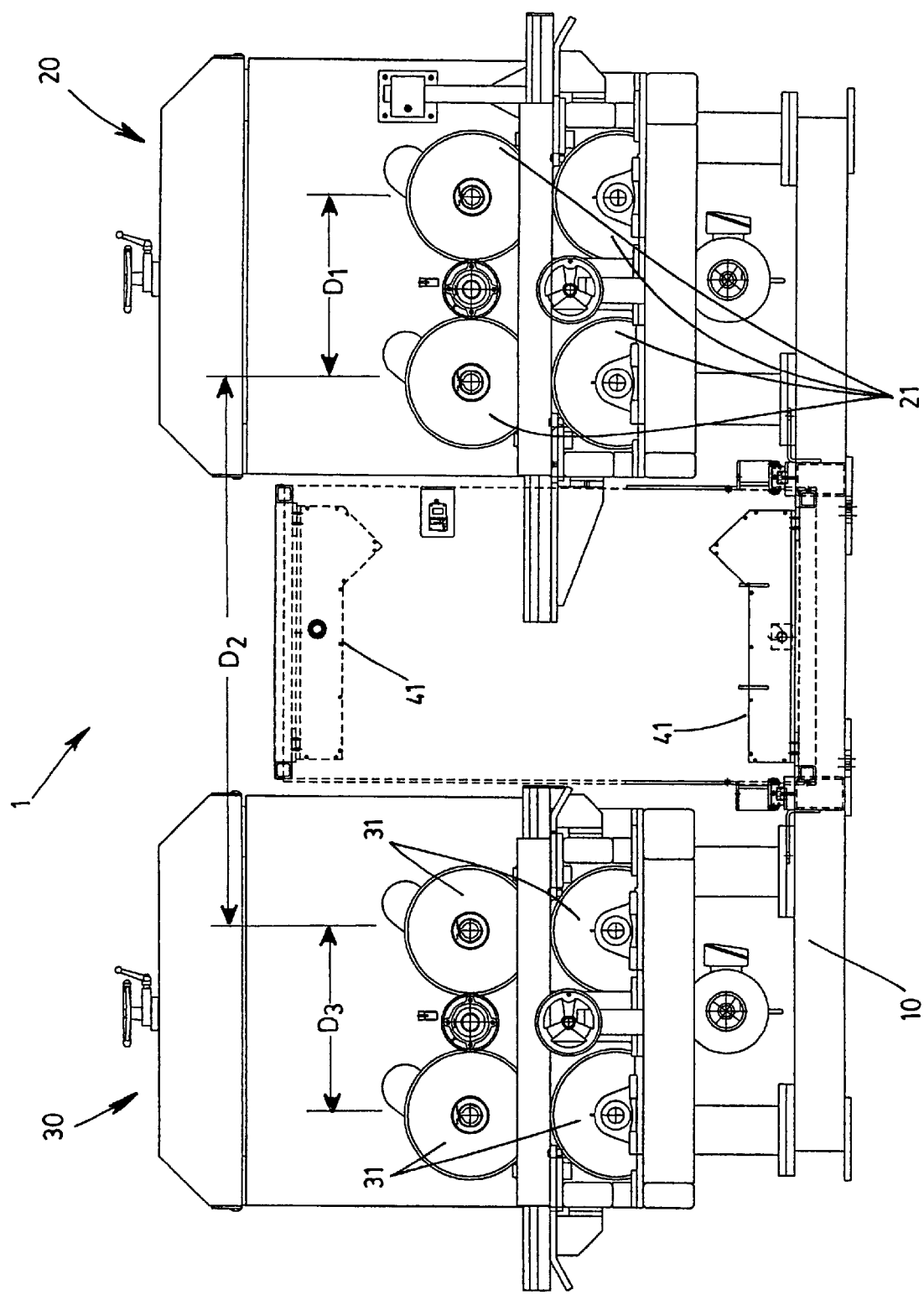
FIG. 1 is a side elevational view of the apparatus according to a preferred embodiment of the present invention.

As can be seen in FIG. 1, the apparatus 1 includes a frame 10 comprising an inlet 20, an outlet 30 and scanning means 40 located between the inlet 20 and the outlet 30. The scanning means 40 includes an output for scanned data.

The inlet 20 comprises at least one roller assembly 21 for securing the piece of wood as it is being fed into the scanning means 40. The inlet may further comprise conveyor means for conveying the piece of wood towards the scanning means.

The outlet 30 also includes at least one roller assembly 31 for securing the piece of wood as it is being fed out of the scanning means 40. The outlet may also comprise a platform for receiving the piece of wood when it is exiting from the scanning means 40.

The apparatus 1 also includes computer means (not shown) operatively connected to the scanning means 40 for receiving the scanned data and processing the data; and control means for controlling the conveyor means and the scanning means to insure proper synchronisation.

One important aspect of the apparatus according to the present invention is that the inlet and outlet roller assemblies 21, 31 are arranged so that at any one time, the piece of wood is being held by at least two points, as will be hereinafter detailed.

In a preferred embodiment, the inlet includes two roller assemblies 21, as better shown in FIG. 1. The roller assemblies each comprises components for holding and guiding the piece of wood at two opposite location on the piece of wood, i.e. two points. Therefore, the piece of wood may be held at its upper and bottom surfaces or at its two opposite side surfaces. This insures proper alignment of the piece of wood throughout its passing in the apparatus. Therefore, according to the preferred embodiment illustrated in FIG. 1, the components of the roller assemblies 21 of the inlet each comprise a top roller and a bottom roller. In this way, the piece of wood is held and guided on its top and bottom surface by the top and bottom rollers, i.e. two points. Since the inlet 20 preferably includes two roller assemblies, the distance between each of the roller assemblies is such that it is smaller that the smallest length of the piece of wood that is to be fed in the apparatus of the present invention. Advantageously, the roller assemblies are longitudinally adjustable, so that the apparatus can analyse pieces of wood of varying lengths.

The inlet includes a U-shaped trough 23 for receiving and guiding a piece of wood. The U-shaped trough is in direct communication with the outlet of the planer. The U-shaped trough has a top and a bottom. Each of them may be provided with roller means (not shown). The width of the trough and the height thereof are adapted to guide and receive a piece of wood. Advantageously, the width and the height can be adjusted so that the apparatus according to the invention can handle pieces of wood of various size. Consequently, the rollers must be adjustable also to account for variations in the thickness of the piece of wood.

In the illustrated embodiment, the outlet 30 has the same configuration as the inlet, except for the fact that the outlet does not include the conveyor means since once the piece of wood has passed through the scanning means, it is ejected at considerable speed. As for the inlet, the outlet may comprise components for holding and guiding the piece of wood at any two opposite location on the piece of wood. Thus, the latter may be held at its upper and bottom surfaces or at its two opposite side surfaces. As detailed above, this insures the proper alignment of the piece of wood throughout its passing in the apparatus. Therefore, according with the preferred embodiment illustrated in FIG. 1, the components of the roller assemblies of the outlet each comprises a top roller and a bottom roller. In this way, the piece of wood is held and guided on its top and bottom surface by the top and bottom rollers, i.e. at two points. Further seen in the illustrated embodiment of FIG. 1 the outlet comprises two roller assemblies. It should be noted that the distance between each of the roller assemblies is preferably such that it is smaller than the smallest length of the piece of wood that is fed in the apparatus of the present invention. Advantageously, the roller assemblies are longitudinally adjustable, so that the apparatus can analyse pieces of wood of varying lengths.

The outlet has a U-shaped trough 33 having a width and a height in direct communication with the scanning means 40. The width and the height of the trough (33) are adapted to guide and receive a piece of wood, and are also preferably adjustable. The U-shaped trough (33) may also include roller means 31.

Consequently, the invention provides an apparatus which holds and guides a piece of wood by at least two points as it passes through the apparatus' top and bottom rollers at the inlet or top and bottom rollers at the outlet. In a preferred embodiment of the invention, the piece of wood is held and guided by at least four points at any time. Therefore, the inlet and the outlet each include two sets of rollers, each set being separated by a distance $D_1$, $D_3$ less than the length of a piece of wood. Further preferably, the distance between the inlet roller adjacent the scanning means and the outlet roller adjacent the scanning means ($D_2$) is less than the length of a piece of wood.

It should be noted that in the event where the spacing between two consecutive pieces of wood fed in the apparatus is not sufficient, the apparatus may not be able to detect the piece of wood as two separate entities and provide adequate results. Accordingly, the rollers are driven at a speed approximately 5% higher than the speed at which said piece of wood is ejected from the planer.

Figure 3:
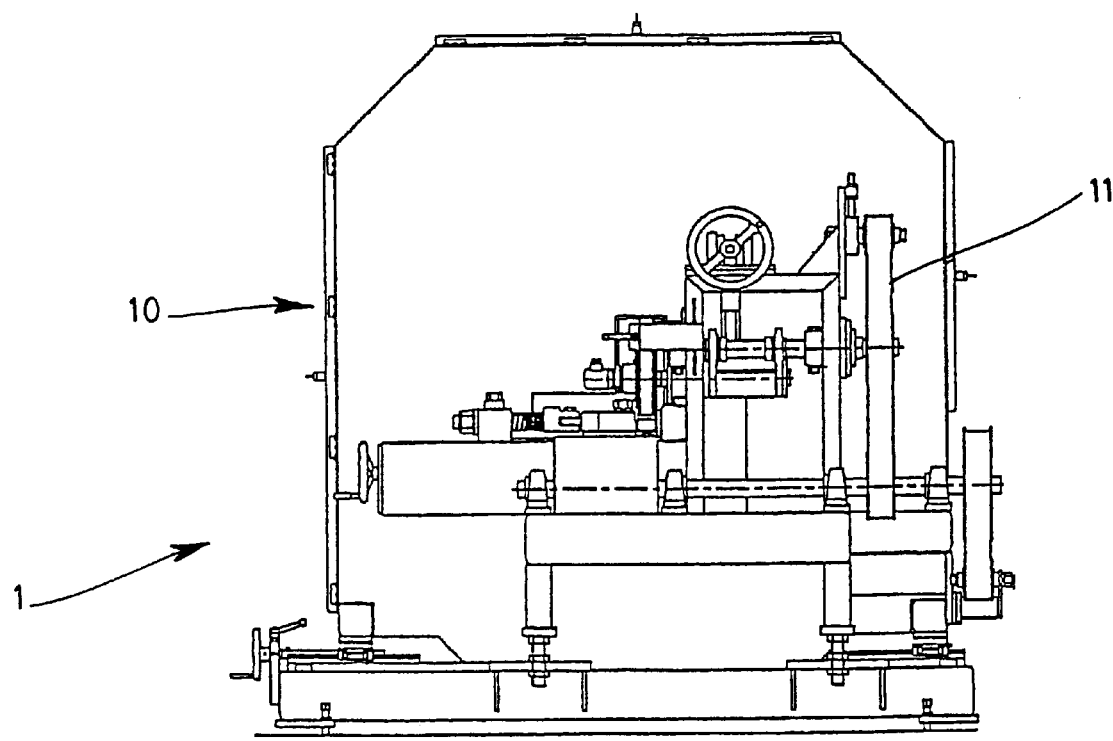
FIG. 3 is a front elevational view of the apparatus of FIG. 1.

As mentioned above, the apparatus also includes control means for controlling the roller assemblies 21, 31 and the scanning means 40 to insure proper synchronisation. To that effect, the rollers are driven either directly or through gears or straps 11 by a motor, which is synchronised with the planer, so that the surface speed of the rollers corresponds to the speed at which the piece of wood is being ejected from the planer (see FIG. 3). If the inlet means also includes conveyor means, the conveyor means also are controlled and synchronised with the motor.

In use, the piece of wood is ejected from the planer and engaged by the inlet means. The inlet means hold the piece of wood and guide it into the scanning means. The piece of wood travels through the scanning means and then is guided into the outlet means, which in turn engage the piece of wood and eject it therefrom for further processing.

The scanning means includes optical means for projecting a beam of light onto the piece of wood as it travels through the scanning means and detection means for receiving the beam of light. The detection means are connected to the output means of the scanning means.

Figure 2:
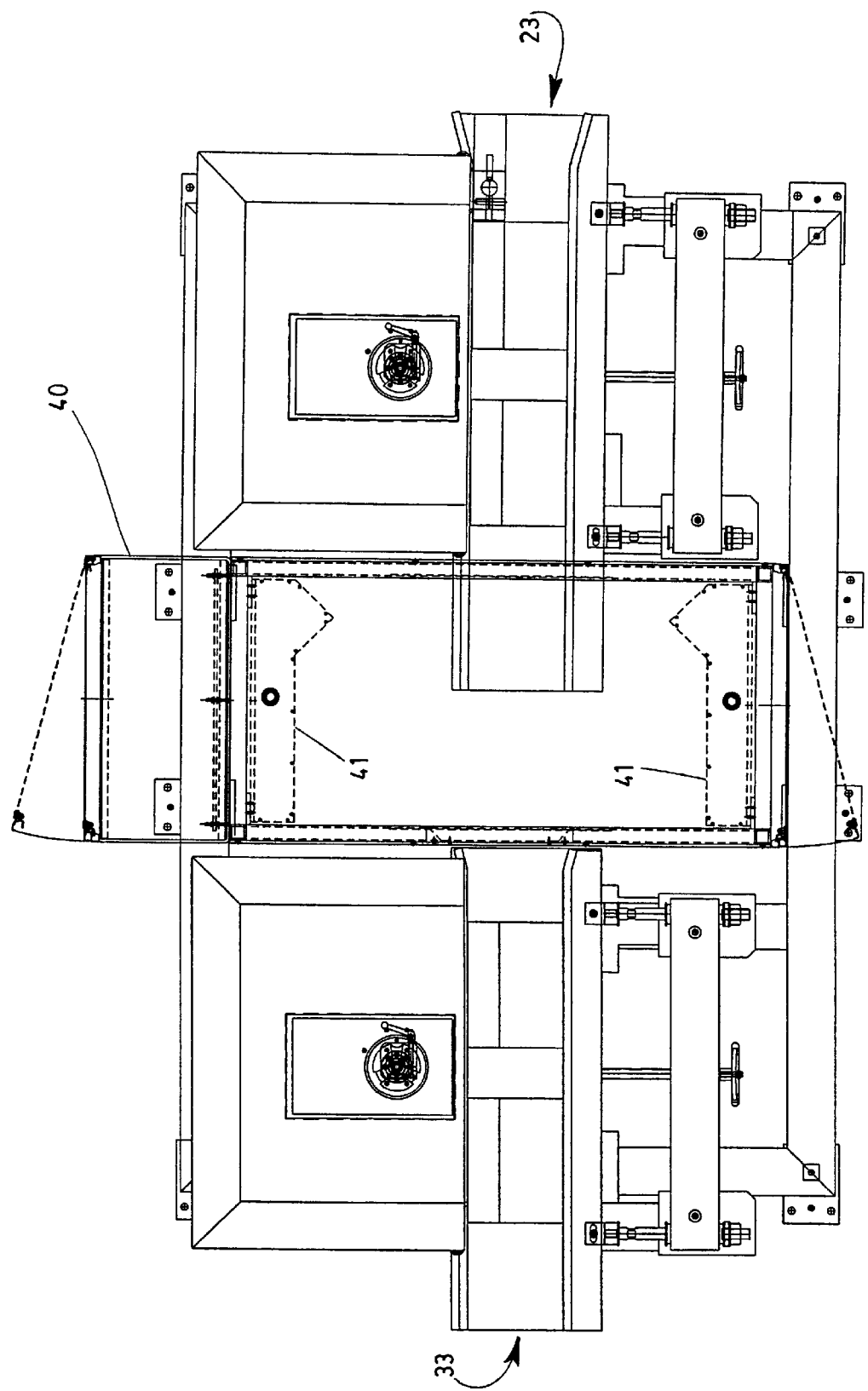
FIG. 2 is a top plan view of the apparatus of FIG. 1.

The scanning means preferably include four lasers 41, each of the lasers being oriented at an angle with respect to each of the four surfaces of the piece of wood (see FIGS. 1 and 2). Therefore, the scanning means is able to view simultaneously all four surfaces of the piece of wood. Each of the lasers has associated therewith a detector, for receiving the light shined on the corresponding surface of the piece of wood. The data collected by each of the detectors is transmitted to a computer means which analyses the data and produces useful information.

More specifically, the data is used to produce a three-dimensional representation of the piece of wood as it is scanned. The three-dimensional representation is then analysed according to various defects (FIGS. 4a to 4e are representative of the various defects which can be recognised by the present invention), and a grading of the piece of wood is then obtained.

The scanning means scan a profile of the piece of wood every one half inch (1.7 cm) with a tolerance of $^{10}/_{1000}$ of an inch.

The purpose of the provision of the roller means is to hold the piece of wood firmly as it is being scanned, which increases considerably the reliability of the scanning means. More specifically, the accuracy of the wane, twist and bow of the piece of wood is far better evaluated when the piece of wood is held as opposed to scanning the piece of wood in a free-standing mode.

In order to further optimise the apparatus of the present invention and subsequent processing of the wood, the apparatus may further be provided with a printer at the outlet thereof, the printed being connected to the computer means and printing a code on the piece of wood for identification purposes. Preferably, the printer is an inkjet printer, and even more preferably an ultraviolet ink printer, so that the wood does not become visibly marked by the printing operation.

It should be noted that the present apparatus can scan approximately 150 pieces of ten feet long wood a minute, or at a rate of approximately 2000 feet a minute.

It should be also noted that the scanning means can further advantageously be provided with an X-ray means for evaluating the degree of rot within the piece of wood or for detecting knots on the piece of wood. It should be understood that additional types of sensors can also be used.

The present invention is also concerned with a process for detecting defects in a piece of wood. The process comprises the steps of feeding a piece of wood in the apparatus according to the
      present invention;
   measuring the length of the wood and registering defects
      of the wood through the scanning means; and
   processing data through the computer means.

Preferably, the results are printed in the form of a code on the piece of wood at the exit of the scanning means.

Although the present invention has been explained hereinabove by way of a preferred embodiment thereof, it should be pointed out that any modifications to this preferred embodiment within the scope of the appended claims is not deemed to alter of change the nature and scope of the present invention.

What is claimed is:

1. An apparatus for detecting surface defects on an elongated piece of wood being conveyed in a scanning direction said scanning direction being parallel to a longitudinal axis of said piece of wood, the apparatus comprising:

a frame comprising
an inlet for loading and conveying the piece of wood in the apparatus in the scanning direction,
an outlet for releasing the piece of wood from the apparatus;
scanning means located between the inlet and the outlet for scanning said piece of wood on all four sides simultaneously, the scanning means including an output for scanned data;
computer means operatively connected to the scanning means for receiving the scanned data and processing said data;
control means for controlling the inlet and the scanning means and insuring proper synchronisation;
the inlet and outlet each comprising at least one roller assembly, each roller assembly being designed to hold the piece of wood on two opposite surfaces thereof so that the piece of wood is conveyed between said roller assembly, each roller assembly further being positioned so that when said piece of wood passes by said scanning means, the piece of wood is held and guided at any point in time by at least two points.

2. An apparatus according to claim 1, wherein the inlet and the outlet each comprise two roller assemblies.

3. An apparatus according to claim 2, wherein the distance between each of the roller assemblies is smaller than the length of the piece of wood.

4. An apparatus according to claim 1, wherein the inlet comprises a conveyor means for conveying the piece of wood in the scanning means.

5. An apparatus according to claim 1, wherein the inlet further comprises a U-shaped trough having a width and a height said width and said height being adjustable, and said trough being adapted to receive and guide the piece of wood entering the apparatus, the U-shaped trough being aligned with the outlet.

6. An apparatus according to claim 1, wherein the outlet comprises a platform for receiving the piece of wood exiting from the scanning means.

7. An apparatus according to claim 1, wherein the outlet further comprises a U-shaped trough having a width and a height, said width and said height being adjustable and said trough being adapted to receive and guide the piece of wood exiting from the scanning means, the U-shaped trough being aligned with the inlet.

8. An apparatus according to claim 1, wherein the rollers are driven at a speed approximately 5% higher than the speed at which said piece of wood is ejected from a planer.

9. An apparatus according to claim 1, wherein the scanning means is further provided with an X-ray means for evaluating the degree of rot within the piece of wood.

10. An apparatus according to claim 1, wherein the apparatus further comprises a printer being connected to the computer means for printing a code on the piece of wood for identification purposes.

11. An apparatus according to claim 10, wherein the printer is an ink jet printer with ultraviolet ink.

12. A method for detecting surface defects of a piece of wood, the method comprises the steps of:

feeding a piece of wood in an apparatus for detecting surface defects, said apparatus comprising:
an inlet for loading and conveying the piece of wood in the apparatus in the scanning direction;
an outlet for releasing the piece of wood from the apparatus;
scanning means located between the inlet and the outlet for scanning said piece of wood on all four sides simultaneously, the scanning means including an output for scanned data;
computer means operatively connected to the scanning means for receiving the scanned data and processing said data;
control means for controlling the inlet and the scanning means and insuring proper synchronisation;
the inlet and outlet each comprising at least one roller assembly, each roller assembly being designed to hold the piece of wood on two opposite surfaces thereof so that the piece of wood is conveyed between said roller assembly, each roller assembly further being positioned so that when said piece of wood passes by said scanning means, the piece of wood is held and guided at any point in time by at least two points;
measuring the length of the wood and registering defects of the wood through the scanning means; and
processing data through the computer means.

13. A method according to claim 12, wherein a code is printed on the piece of wood at the exit of the scanning means.

* * * * *